United States Patent [19]

Hass

[11] 4,194,288
[45] Mar. 25, 1980

[54] ARTIFICIAL TEETH THAT MINIMIZE STRESSES ON DENTURE SUPPORTING TISSUE

[75] Inventor: Martin A. Hass, 1105 El Medio Dr., Pacific Palisades, Calif. 90272

[73] Assignee: Martin A. Hass, Los Angeles, Calif.

[21] Appl. No.: 875,300

[22] Filed: Feb. 6, 1978

[51] Int. Cl.² ............................................... A61C 13/00
[52] U.S. Cl. ..................................... 433/197; 433/202
[58] Field of Search ........................................... 32/2, 8

[56] References Cited

U.S. PATENT DOCUMENTS 990,548  4/1911  Gysi ............................................ 32/8
3,027,642  4/1962  Strack ......................................... 32/8

Primary Examiner—Robert Peshock

[57] ABSTRACT

Artificial posterior teeth of non-interlocking construction having flat surfaces parallel to the plane of lateral tooth movement that form a major portion of the occlusal surfaces. Since the teeth can freely slide laterally on one another, side stresses that would tend to shift the dentures are avoided, even though a cross-bite setup is used. Each tooth has a laterally extending, food positioning and holding groove and one or more spillways thereon that permit fluids and comminuted food to escape, thereby reducing hydraulic pressure.

8 Claims, 5 Drawing Figures

ARTIFICIAL TEETH THAT MINIMIZE STRESSES ON DENTURE SUPPORTING TISSUE

BACKGROUND OF THE INVENTION

The present invention relates to artificial teeth, and more particularly to posterior teeth having a novel non-interlocking shape that minimizes harmful side stresses and lateral shifting of dentures.

Most previously known artificial teeth are essentially imitations of natural teeth insofar as their configuration is concerned, taking advantage of the efficient biting and chewing surfaces of interlocking cusps that are the product of evolution. There are, however, certain well known problems associated with these immitative or anatomical artificial teeth, largely attributable to the fact that they are not firmly anchored in the mouth, as in the case of natural teeth. The lower denture in particular is not held as securely as desired because the tongue divides the area between the left and right gum ridges that would otherwise provide a suction surface. Movement or wobble of the dentures causes soreness, food packing, physiological deterioration of gum tissue and increased looseness, these problems being very serious in many cases.

One proposed artifical tooth construction, described in my U.S. Pat. No. 3,060,576, utilizes teeth that are shaped to provide stabilizing forces directed toward the lingual side of the lower teeth. Like other previously known arrangements, it employs interlocking cusps after the manner of natural teeth, the stabilizing forces being produced by the inclined orientation of mutually engaging surfaces.

It has been found that substantial undesired lateral shifting of the dentures is attributable to side stresses. When interlocking cusp teeth are used, these stresses may be caused, even when not chewing, by sideways movement of the lower jaw and transformation of vertical forces into horizontal forces by inclined tooth surfaces.

A primary objective of the invention is to provide artificial posterior teeth that minimize undesirable side stresses, thereby reducing or eliminating undesired denture shifting and physiological problems, such as impaired temporo-mandibular joint function.

SUMMARY OF THE INVENTION

The present invention comprises a setup of one or more artificial posterior teeth, each having a flat surface forming a portion of its occlusal or chewing surface and lying within the plane of lateral tooth movement. This flat surface engages a similar flat surface on a vertically opposed tooth so that the teeth do not interlock but are free to slide cross-wise on each other with only minimal or negligible side stresses being introduced. A channel for positioning and holding food bolus for mastication extends laterally along the occlusal surface of each tooth from one end to the other. The preferred teeth also define spillways that extend across the flat surfaces to the channels to provide for the escape of fluid and comminuted food, thereby reducing the hydraulic pressure.

The side surfaces of the lower tooth channels, which may be generally V-shaped in cross-section, should preferably intersect along a line closer to the lingual side when compared to the intersection line of the overlying upper channels, thereby producing stabilizing forces directed toward the lingual side of the lower denture when material positioned in the channels is compressed.

Other features and advantages of the present invention will be apparent from the following detailed description, taken in conjunction with the accompanying drawing in which:

DESCRIPTION OF THE PREFERRED EMBODIMENT

Figure 1:
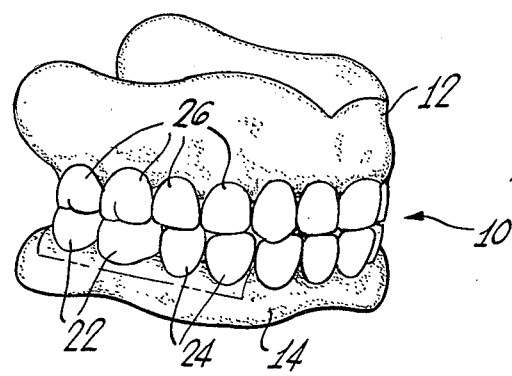
FIG. 1 is a perspective view of an exemplary pair of artificial non-crossbiting dentures constructed in accordance with the present invention, shown in their natural closed position but removed from the mouth.
Figure 2:
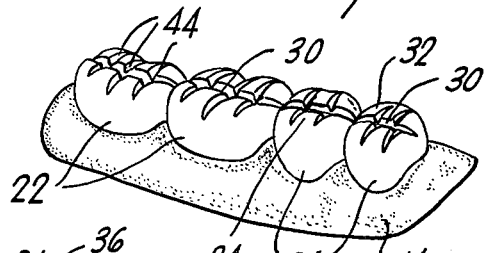
FIG. 2 is a perspective view of the two lower molars and two bicuspids located within the indicated area of FIG. 1.

A pair of artificial dentures 10 that embody many novel features of the present invention, shown in FIGS. 1-4 of the accompanying drawings, includes upper and lower denture base members 12 and 14 molded to fit the gum ridges 16 and colored to simulate natural gums. The upper base member 12 is part of the upper denture which underlies the roof of the mouth and is relatively firmly positioned, in the conventional manner, by this large suction surface. The lower denture, which includes the lower base member 14, is generally U-shaped to surround the tongue 20 and, because it employs a considerably smaller suction surface, is more susceptible to shifting or wobbling. Among the undesirable effects of this looseness of the lower denture 14 is a tendency to soreness, food packing and a degeneration of the underlying gum ridge 16 that contributes in turn to further looseness.

Principal causes of denture shifting are lateral movement of the lower jaw, transformation of vertical forces into horizontal forces and non-alignment of the differently shaped upper and lower gum ridges. Side stresses resulting from all these causes are, however, minimized or eliminated by the unique non-interlocking construction of the posterior teeth, including two molars 22 and two bicuspids 24 on each side, shown separately in FIGS. 2 and 4. It will be understood that the vertically opposing upper teeth 26 are of generally similar configuration insofar as these occlusal surfaces are concerned.

Each posterior tooth 22, 24, 26 has a body portion which is wider at the base than on the biting surface so that it is held and firmly gripped by one of the denture bases 12 or 14 in which it is imbedded. It has a flat upper surface 28 in the normally horizontal plane of lateral or cross-wise tooth movement. This flat surface 28 forms a major portion of the occlusal surface, i.e., the chewing surface of the tooth 22, 24. The occlusal surfaces of the teeth 22, 24 do not at any point extend beyond the flat surfaces 28 so that when the upper and lower teeth 22, 24 and 26 come together, the opposing flat surfaces are free to slide on each other without producing the side stresses that would result if the teeth were of a conventional, pseudo-anatomical, interlocking configuration.

To position a bolus of food on the occlusal surfaces for comminution, each tooth 22, 24 has a channel 30 extending from one end of the tooth to the other (an end of a tooth being defined as the generally vertical surface that opposes a vertical surface of an adjacent tooth), dividing the flat surface 28 into two separate portions, a buccal or outer portion 32 and a lingual or inner portion 34.

Figure 3:
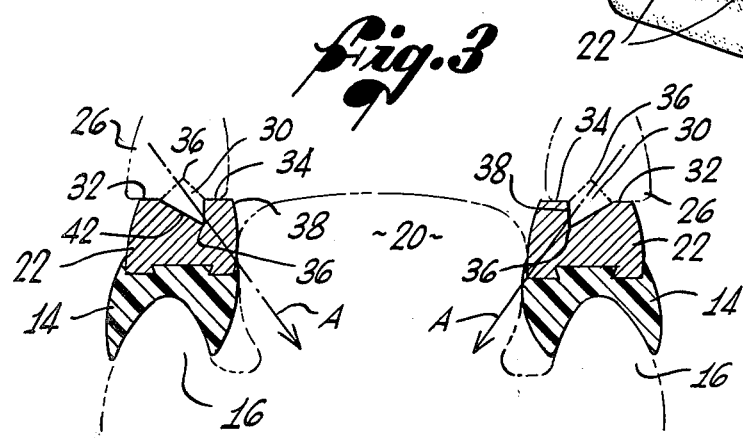
FIG. 3 is a cross-sectional view of the lower denture of FIG. 1, the teeth of the upper denture being indicated in phantom outline, as are the gum ridges and tongue of the wearer.
Figure 4:
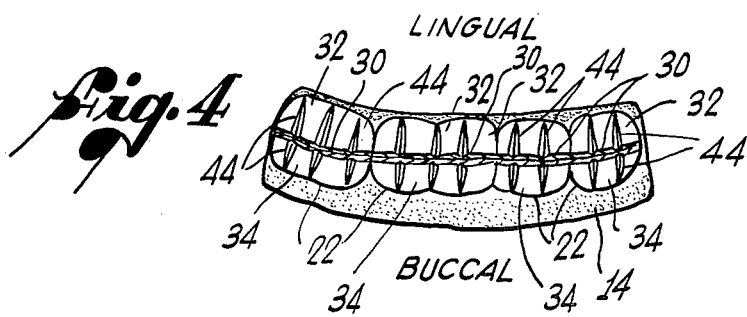
FIG. 4 is a top elevational view showing occlusal surfaces of the teeth of FIG. 2.

The channels 30 are of generally V-shaped cross-section, as best shown in FIG. 3, having two side surfaces that meet along a line of intersection 36 at which the channel depth is at a maximum. In the lower teeth 22, 24, however, the lingual or tongue surface 40 of the channel 30 is relatively vertical while the buccal surface 42 is inclined more to the horizontal. The upper teeth 26 have channels 30 of almost symmetrical cross-section with the line of intersection 36 slightly closer to the buccal or cheek side, so that the intersection line 36 of the lower channel is substantially offset closer to the lingual side when compared to an overlying upper channel. When bolus of food or other material within the channels 30 is subjected to compressive forces, the resulting force applied to the lower plate 14 is not vertical but is sharply inclined downwardly and inwardly over the crest of the gum ridge 16 and toward the lingual side. It, therefore, produces a torque tending to rotate the lower denture 14 so that it presses against the gum ridge 16 on the opposite side of the mouth. This inwardly directed force (represented by arrows A in FIG. 3) is, therefore, a stabilizing force that counteracts the tendency of the lower denture to rotate and lift off the gum ridge 16, particularly when mastication takes place on only one side at a time.

Both the upper and lower posterior teeth 22, 24 and 26 are provided with spillways 44 that extend across the buccal and lingual portions 32 and 34 of the flat surfaces 28 and intersect the channels 30 perpendicularly. These sluiceways 44 allow comminuted foods and fluids to escape from the channels 30, thereby reducing the hydraulic pressure and the forces applied to the gum ridges 16. If these forces were permitted to build up on the occlusal surface, they would contribute to gum soreness and bone shrinkage.

It is important to note that when conventional interlocking teeth are employed, the required position of the upper teeth with respect to the lower teeth is predetermined by the configuration of the biting surfaces that must match. It is therefore impossible, in most cases, for both the upper and lower posterior teeth to be set directly over the respective gum ridges, which are not aligned. When teeth are offset substantially with respect to the gum ridge, certain instability results. An important advantage of the non-interlock teeth of the present invention is that they can be set directly on the gum ridges, following its natural ridge curvature, for maximum stability and chewing efficiency.

Figure 5:
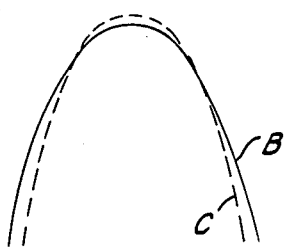
FIG. 5 is a schematic diagram showing the superimposition of typical upper and lower dental arches.

A typical gum ridge configuration is illustrated schematically in FIG. 5. The upper arch is narrower at the back so that it crosses over the lower arch. Accordingly, the upper posterior teeth, mounted directly over the gum ridge in the preferred setup, cross the lower posterior teeth in an X-like, modified cross-bite pattern which produces maximum biting power, stability and a natural appearance. In FIG. 5, the centerline of the lower teeth is represented by the solid line B while the center line of the upper teeth is represented by the broken line C.

It will be appreciated that the dentures of the present invention greatly reduce the undesirable side stresses produced by the interlocking of previously known artificial teeth. Nevertheless, bolus can be grasped and positioned for mastication by the channels 30 and excessive hydraulic pressure is eliminated by the spillways 44. A highly desirable grinding action results, along with free lateral movement that most denture wearers prefer.

While the invention has been described in connection with a specific embodiment, it will be apparent to those skilled in the art that modifications and changes can be made without departing from the spirit and scope of the invention as defined by the appended claims.

I claim:

1. An artificial posterior tooth that minimizes side stresses comprising:
   a substantially flat surface forming a major portion of the occlusal surface and lying within the plane of lateral tooth movement;
   a channel for positioning bolus of food extending along the occlusal surface from one end of said tooth to the other, said channel dividing said flat surface into buccal and lingual portions; and
   at least one spillway extending across at least one of said portions of said flat surface to said channel, thereby permitting the escape of fluids and comminuted material.

2. An artificial tooth as defined in claim 1 in which there are a plurality of spillways each of which extends across one of said surface portions perpendicular to said channel.

3. A pair of cooperating artificial dentures that minimize side stresses comprising:
   an upper denture base member;
   at least one artificial posterior upper tooth having a body portion anchored in said upper denture base member;
   a lower denture base member; and
   at least one artificial posterior lower tooth having a body portion anchored in said lower denture base member, said lower tooth being oriented and positioned for engagement by said upper tooth;
   said upper and lower teeth having non-interlocking configurations to prevent the transmission of side stresses from one of said teeth to the other, said teeth defining substantially flat and parallel opposing surfaces within the plane of lateral tooth movement, at least some of said teeth defining a positioning channel extending from one end thereof to the opposite end thereof, said channel dividing said flat surface of said teeth into separated buccal and lingual portions.

4. A pair of dentures as defined in claim 3 in which each of said teeth defines a spillway extending across at least one of said portions of said flat surface to one of said channels, thereby permitting the escape of fluids and comminuted material and reducing the hydraulic pressure produced during mastication.

5. A pair of dentures as defined in claim 4 in which said channels overlie each other when said upper and lower teeth are mutually engaged, the configuration of said channels being such that compressive forces exerted on material within said channels result in a stabilizing force applied to said lower tooth and directed toward the lingual side of said lower tooth.

6. A pair of dentures as defined in claim 5 in which each of said channels is generally V-shaped.

7. A pair of dentures as defined in claim 5 in which each of said channels has two sides that meet along an intersection line of maximum channel depth, the intersection line of said lower tooth being offset toward the lingual side when compared to the intersection line of said upper tooth, whereby compressive forces exerted on material within said channels result in a stabilizing force applied to said lower tooth and directed toward the lingual side of said lower tooth.

8. A pair of cooperating artificial dentures that minimize side stresses comprising:
   an upper denture base member;
   a plurality of artificial posterior upper teeth each having a body portion anchored in said upper denture base member;
   a lower denture base member; and
   a plurality of artificial posterior lower teeth each having a body portion anchored in said lower denture base member, said lower teeth being arranged for engagement by said upper teeth;
   said upper and lower teeth having non-interlocking configurations to prevent the transmission of side stresses, said teeth defining:
   substantially flat and parallel opposing surfaces extending along the occlusal surfaces thereof and lying within the plane of lateral tooth movement;
   a channel of generally V-shaped cross-section extending along each tooth from one end thereof to the opposite end thereof and dividing said flat surface of said tooth into separated buccal and lingual portions, the channels of said upper teeth overlying the channels of said lower teeth, said channels serving to position bolus of food, each of said channels having two sides that meet along an intersection line of maximum channel depth, the intersection line of said lower teeth being offset toward the lingual side when compared to the intersection line of said upper teeth, whereby compressive forces exerted on material within said channels results in stabilizing forces applied to said lower teeth and directed toward the lingual side of said lower teeth to produce a cross-stabilizing force on the denture base in which it is mounted when chewing food; and
   a plurality of spillways extending across at least some of said portions of said flat surfaces to said channels, thereby permitting the escape of fluids and comminuted material.

* * * * *